United States Patent [19]

Fairbanks et al.

[11] 4,088,500

[45] May 9, 1978

[54] WATER EXTENDED HYDROPHILIC MOLDING COMPOSITIONS

[75] Inventors: Charles W. Fairbanks, Little Canada; John F. Kistner, Afton, both of Minn.

[73] Assignee: Minnesota Mining and Manufacturing Company, Saint Paul, Minn.

[21] Appl. No.: 386,984

[22] Filed: Aug. 9, 1973

Related U.S. Application Data

[63] Continuation of Ser. No. 128,172, Mar. 25, 1971.

[51] Int. Cl.$^2$ .............................................. C09K 3/00
[52] U.S. Cl. .............................. 106/35; 260/29.2 TN; 260/29.4 R; 260/37 N; 260/37 AL
[58] Field of Search ............... 260/29.4 R, 77.5 AM, 260/858, 29.2 TN, 37 N, 857 F, 37 AL; 106/35; 264/16

[56] References Cited

U.S. PATENT DOCUMENTS

| | | | |
|---|---|---|---|
| 3,184,426 | 5/1965 | Thoma et al. | 260/77.5 SP |
| 3,329,655 | 7/1967 | Emmons et al. | 260/29.4 R |
| 3,384,606 | 5/1968 | Dieterich et al. | 260/29.4 R |
| 3,557,044 | 1/1971 | Bleasdale et al. | 260/77.5 AM |

*Primary Examiner*—Lorenzo B. Hayes
*Attorney, Agent, or Firm*—Cruzan Alexander; Donald M. Sell; Gary L. Griswold

[57] ABSTRACT

Molding compositions useful for molding water-extended hydrophilic articles are provided which are tough, soft and form-stable and comprise, generally, an amide-endcapped hydrophilic alkylene oxide polymer, a crosslinking agent, water, and a filler. The composition is cured by means of an acid catalyst. The compositions are useful in the preparation of denture liners which exhibit excellent adhesion to denture plates and provide structural stability, toughness and softness.

6 Claims, No Drawings

WATER EXTENDED HYDROPHILIC MOLDING COMPOSITIONS

This is a continuation, application Ser. No. 128,172 filed Mar. 25, 1971.

BACKGROUND OF THE INVENTION

The present invention relates to molding compositions useful for the preparation of water extended hydrophilic molded articles that are soft but yet structurally stable, tough and readily machined and polished. More particularly, the present invention relates to soft denture liners prepared from the molding composition which provide a soft cushion between the dental plate and the user's gums and which exhibit good adhesion to a dental plate, toughness, and superior structural stability. Still more particularly, the present invention relates to soft denture liners fabricated of water-extended, filled, crosslinked amide-endcapped alkylene oxide polymers.

At present, denture liners are utilized on a denture plate to provide a soft, smooth but firm contact with the user's gum so that the gums are not irritated by the plate. Various materials have been employed for this purpose, among which are plasticized waxes, polyvinyl chloride, soft acrylic polymers, silicone elastomers and hydrogels based on poly β-(hydroxyethyl)methacrylate, commonly referred to as "Sofdent". Denture liners prepared of these materials have a short lifetime and are unsatisfactory for one or more other reasons. The wax liners are fragile and easily damaged. Liners of plasticized polyvinyl chloride are difficult to fabricate and the plasticizer migrates from the liner into the plate causing the liner to harden and crack and the plate to soften and deform. Soft acrylic liners have poor adhesion to the dental plate base and have low abrasion resistance. Silicone elastomer liners are difficult to fabricate and polish, take on stain, and may foul during use. The "Softdent" liners tend to pick up about 50% by weight of water upon soaking therein and undergo dimensional changes so that precise impressions made by the dentist no longer fit the wearer's mouth.

Consequently, there are no soft denture liners known to the applicants that are tough, comfortable, exhibit good dimensional stability and have a long life and yet are easy to fabricate and finish when on the dental plate.

SUMMARY OF THE INVENTION

According to the present invention, there are provided certain molding compositions comprising an amide-endcapped alkylene oxide polymer, an acid activated cross-linking agent, water, and a suitable filler. The compositions may be molded to tough, soft, form-stable, water-extended, cross-linked products such as denture liners. Denture liners prepared according to the present invention may be fabricated under presently known procedures employed in dental clinics. The denture liners exhibit excellent dimensional stability and toughness and, when mounted on dental plates, are comfortable and non-irritating. The denture liners are preferably prepared by curing the compositions of the invention in place on dental plates. The denture liners so prepared have the necessary qualities of softness required for firm fitting, comfort and exhibit excellent adhesion to dental plates, particularly the commonly used acrylic denture bases when applied over a primer based on polyisocyanates, but yet can be finished by grinding and polishing procedures normally used on denture plates.

The molding composition for use in the preparation of the soft denture liners of the present invention comprises, generally, an hydrophilic amide-endcapped alkylene oxide polymer; a melamine crosslinking agent, water, and a suitable filler. Preferably, for each 100 parts of the polymer, about 2 to 8 parts crosslinking agent 25 to 50 parts water, and about 20 to 45 parts filler are used.

More preferably, the composition useful in the preparation of the soft denture liners of the present invention comprises:

(a) An amide-endcapped hydrophilic alkylene oxide prepolymer having the formula

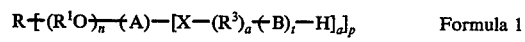

Formula 1 wherein R is a polyvalent organic residue of an organic alkyl compound having $p$ reactive hydrogens but devoid of such hydrogens; $(R^1O)$ is a hydrophilic polyalkylene oxide chain having a plurality of ethylene oxide units; $n$ is an integer from about 5 to 25; A is a polyvalent hydrocarbyl residue of an organic polyisocyanate having $a +1$ reactive groups; X may be —O—,

or —S— wherein $R^2$ is hydrogen or a lower alkyl group having 1 to 6 carbon atoms; $R^3$ is a radical selected from the group consisting of divalent hydrocarbyl groups including alkylene, arylene, and alkarylene groups; $s$ may be 0 or 1 and when $s$ is 0, B is a divalent radical having the formula

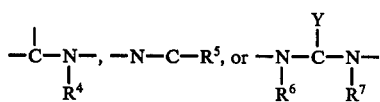

and when $s$ is 1, B may additionally have the formula

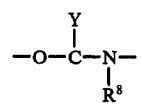

wherein Y is a divalent oxygen or sulfur, $R^4$, $R^5$, $R^6$, $R^7$ and $R^8$ are selected from the group consisting of hydrogen, lower alkyl having from 1 to 6 carbon atoms, and phenyl, and $R^6$ and $R^7$ together with the nitrogen atom may form a ring having from 4 to 7 atoms therein; $t$ is 0 or 1; $a$ is an integer from 1 to 3; and $p$ is an integer from 2 to 6;

(b) From 2 to 8 parts of an acid activated crosslinking agent selected from the group consisting of aliphatic aldehyde progenitors and compounds having the formula

Formula 2 wherein $R^9$ is a polyvalent organic nitrogeneous residue selected from the group consisting of

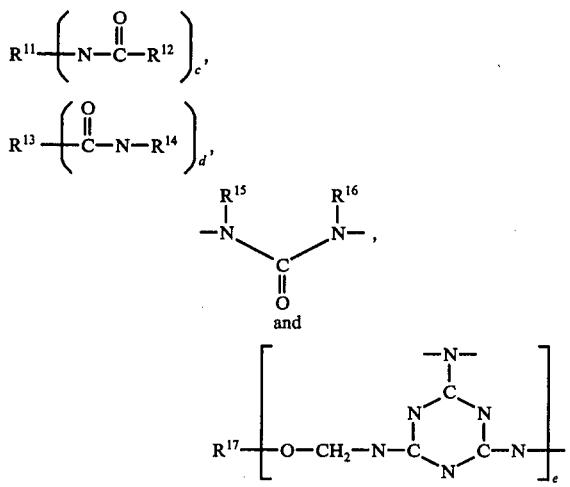

wherein $R^{11}$ and $R^{13}$ are polyvalent organic residues having a combining valency of $c$ and $d$ respectively; $c$ and $d$ are integers having a value of from 2 to 4; $R^{12}$, $R^{14}$, $R^{15}$, and $R^{16}$ are selected from the group consisting of hydrogen and lower alkyl groups having from 1 to 6 carbon atoms, and $R^{14}$ and $R^{15}$ together may form a ring with the nitrogen atom having 4 to 7 atoms therein; $R^{17}$ is a polyvalent radical of an organic polyhydroxy alkyl compound having $e$ hydroxyl groups but devoid of such groups, $e$ is an integer from 1 to 6; and where $e$ is 1, $R^{17}$ is a lower alkyl group having from 1 to 6 carbon atoms; $R^{10}$ is a lower alkyl group having from 1 to 6 atoms; and $b$ is an integer from 2 to 6;

(c) From 20 to 50 parts by weight of water;
(d) From 20 to 45 parts by weight of a suitable filler; and
(e) From 0.1 to 3 parts by weight of a catalyst selected from the group consisting of acids having a $pK_a$ less than 4, and latent acid generating compounds capable of generating an acid having a pKa less than 4 upon heating at a temperature of at least 50° C.

In the formula for the prepolymer, $t$ is 0 only when X is $$-\underset{R^2}{N}-$$

and $s$ is 0.

The term "active hydrogen" used in the above description is well known and commonly used in the art, and as used herein means active hydrogen as measured and determined by the method described by Zerewitinoff, J. Am. Chem. Soc., 49, 3181 (1927).

The amide-endcapped prepolymers used in the compositions of the invention may be prepared in accordance with the following steps:

a. preparing a functionally reactive group-terminated polyalkylene oxide prepolymer by reaction of a hydrophilic polyalkylene oxide polyol having a plurality of ethylene oxide units with an excess of polyisocyanate and b. endcapping the functionally reactive group terminated polyalkylene oxide prepolymer by reaction with a compound selected from compounds having the formula $$H-X-R^3-BH$$

wherein X, $R^3$, and B have the meaning defined heretofore.

The molding compositions of the invention are a mixture of a major amount of the amide-endcapped prepolymers and a minor amount of the acid catalyzable crosslinking agent. The compositions are cured by adding a minor amount of a catalyst comprising an acid or a latent acid generating compound to the composition. The acid added or generated may have a dissociation constant, ($pK_a$), less than 1, such as the aromatic sulfonic acids, perfluorocarboxylic acids and mineral acids, (e.g., sulfuric acid, perchloric acid, hydrochloric acid, and phosphoric acid, and the like) or it may be an acid having $pK_a$ values up to about 4. Generally, the higher the pKa value the higher the temperature and/or longer the time required to effect the cure of the composition. Latent acid generating compounds are also useful by providing acids, upon heating, having a $pK_a$ of less than about 4. Examples are substituted amine hydrochloride salts, and certain alphahaloketones.

In a preferred embodiment of the invention the molding composition is stored as a two part system; the parts being mixed prior to molding. In the two part system, one part contains a certain portion of the hydrophilic alkylene oxide prepolymer, water, filler, and the crosslinking agent and the other part contains the remainder of the prepolymer, water, filler, and the acid catalyst. Since the components of the two parts are hydrolytically stable, the two parts have an almost indefinite shelf life. Soft, tough, water-extended, hydrophilic, form-stable moldings are made by mixing the two parts of the composition, placing the mixed composition into a mold and heating the mold for a sufficient time to effect cure.

The hydrophilic polyalkylene oxide polyols that may be used in the preparation of the compositions of the invention may be prepared in a manner well known in the art by the reaction of an organic reactive hydrogen containing compound with alkylene oxides. Illustration of the organic reactive hydrogen containing compounds that may be used include, among others, ethylene glycol; 1,2-propanediol; 1,3-propanediol; 1,3-butanediol; 1,4-butanediol; glycerol, 1,2,4-butanetriol; 1,2,6-hexanetriol; 1,2,3-trimethylolpropane, 1,1,1-trimethylolpropane; pentaerythritol, sorbitol, mannitol, diethyleneglycol; triethyleneglycol; and the like. Other reactive hydrogen compounds that may be used include polyamines, e.g., ethylene diamine, propylenediamine, hexamethylenediamine, diethylenetriamine, triethylenetetraamine; and polythiols, e.g., ethylenedithiol, propylenedithiol, and 1,2,3-propanetrithiol.

The hydrophilic polyalkylene oxide polyols are prepared by reacting the organic reactive hydrogen compound, having from 2 to 6 reactive hydrogens with from about 5 to about 25 alkylene oxide equivalents per reactive hydrogen. At least 50% of the alkylene oxide equivalents must be ethylene oxide. The remaining alkylene oxide may be propylene oxide. An example of a preferred hydrophilic polyalkylene oxide polyol is prepared from trimethylolpropane and ethylene oxide and has the structure:

| | | |
|---|---|---|
| $CH_3CH_2C$ | $CH_2O\ (CH_2CH_2O)_xH$ $CH_2O\ (CH_2CH_2O)_yH$ | Formula 3 |

-continued

CH$_2$O (CH$_2$CH$_2$O)$_x$H

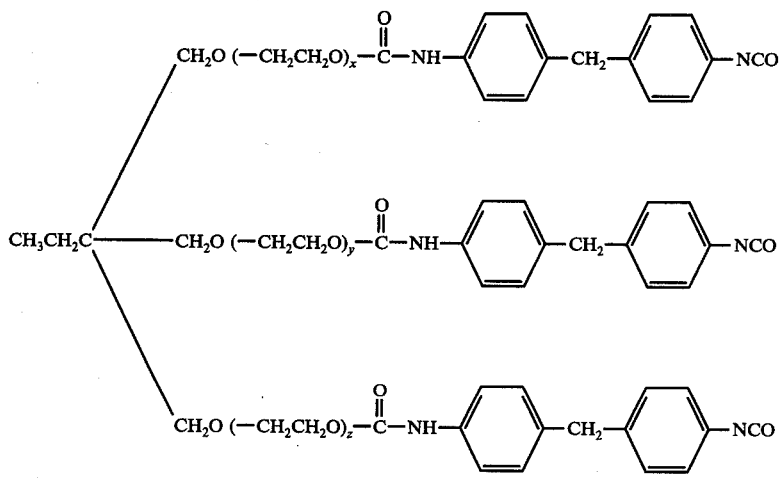

wherein x, y and z are integers of from 5 to 25.

Commercially available polyalkylene oxide polyols that may be used are the hydrophilic ethylene oxide-propyleneoxide block copolymer polyols commercially available from Wyandotte Chemical Co. under the trademark "Pluronic" such as Pluronic L35, F38, and P46, and the hydrophilic ethylene oxide-propylene oxide random copolymer polyols available from Jefferson Chemical Co., under the tradename "Polyol Functional Fluids" such as WL260, WL360, and WL580.

Generally, the hydrophilic or water soluble polyalkylene oxide polyols that may be used have molecular weights of at least 600 and as high as 3000. Preferably they are polyethylene oxide triols having molecular weights between about 1150 and 1500.

The isocyanate-terminated prepolymers useful in preparing the compositions of the invention are the reaction products of the polyisocyanates, having an isocyanate functionality of 2 to 6, and the hydrophilic polyalkylene oxide polyols described above. Methods of preparing the isocyanate terminated prepolymers are disclosed in the art; for example, see U.S. Pat. Nos. 2,726,219 and 2,948,691 and "Polyurethanes: Chemistry and Technology," by Saunders & Frisch, Part I, Interscience Pub., N.Y. (1962). Generally such a prepolymer is prepared by reaction of a polyalkylene oxide polyol with a polyisocyanate using a NCO/OH equivalent ratio of at least 2/1 and preferably slightly higher than this, e.g., 2.1/1 to 2.5/1.

Polyisocyanates that may be used include, for example, ethylene diisocyanate, propylene-1,2-diisocyanate; butylene-1,4-diisocyanate; hexamethylene-1,6-diisocyanate, cyclohexylene-1,2-diisocyanate; m-phenylene diisocyanate, mixtures of toluene-2,4-diisocyanate and toluene-2,6-diisocyanate; diphenyl-3,3'-dimethyl-4,4'-diisocyanate; diphenyl-3,3'-dimethyoxy-4,4'-diisocyanate; diphenylmethane-4,4'-diisocyanate; diphenylmethane-4,4'-dimethyl-3,3'-diisocyanate; dicyclohexylmethane-4,4'-dimethyl-3,3'-diisocyanate; 1,5-naphthalene diisocyanate; and polymethylene polyphenylene-polyisocyanates such as the commercially available "Papi," from the Upjohn Company.

An example of a preferred isocyanate-terminated prepolymer is the prepolymer prepared by the reaction of the hydrophilic polyalkylene oxide polyol described heretofore and diphenylmethane-4,4'-diisocyanate. The functionally reactive group-terminated prepolymer has the structure:

wherein x, y and z are integers having a value of 8 to 10.

The functionally reactive group-terminated prepolymers are endcapped by reaction with at least an equivalent amount of a compound having a hydrogen atom reactive with the reactive group of the prepolymer, and either having an amide group in the compound or forming an amide group. In either case, the amide group of the compound or the formed amide group must have a less reactive hydrogen atom than the hydrogen atom employed for reaction with the isocyanate-terminated prepolymer, and capable of reacting with a crosslinking agent.

Compounds that may be used to endcap the reactive group-terminated prepolymers of the invention include amines, e.g., ammonia, methylamine, ethylamine, n-hexylamine, and aniline; -hydroxyacylamides, e.g., glycolamide, salicylamide, aminoacylamides, e.g., glycinamide, N-methylglycinamide, N-hexylglycinamide, and N,N'-dimethylglycinamide; -thiolacylamides, e.g., thioacetamide, -thiolbutyramide, and -thiol-N-methyl-butyramide; N-acylaminolalkanols, e.g., N-acetylethanolamine, N-butyrylethanolamine, and 4-(N-acetylamino)-butanol; monoacylalkylene-diamines, e.g., acetylethylenediamine, propionylethylenediamine, and acetylbutylenediamine, acylaminomercaptans, e.g., acetylaminobutyl mercaptan; substituted ureas, e.g., N-(2-hydroxyethyl)-N-methylurea, N-(2-hydroxyethyl)-N,N'-dimethyurea, N-(3-hydroxypropyl)-N-methylurea, N-(6-hydroxyhexyl)urea, N-(4-hydroxycyclohexyl)-urea N-(2-aminoethyl)-N-methylurea, and N-(2-methylaminoethyl)-N,N'-dimethylurea; thiol ureas, e.g., N-(2-mercaptoethyl)urea; thioureas, e.g., N-(2-hydroxyethyl)-N-methylthiourea, and N-(2-mercaptoethyl)-N,N'-dimethylthiourea; alkyleneureas, e.g., N-(2-hydroxyethyl)imidazolidone, N-(3-hydroxypropyl)-imidazolidone, N-(4-hydroxybutyl)imidazolidone, N-(6-hydroxyhexyl)-imidazolidone, N-(4-hydroxycyclohexyl)imidazolidone, N-(2-hydroxyethyl)uretidinone, N-(2-hydroxyethyl)uretidinone, N-(2-hydroxyethyl)hexahydroxyprimidinone-2, N-(2-hydroxyethyl)-hexahydro-1,3-diazepinone-2, N-(2-methylaminoethyl)imidazolidone, N-(2-aminoethyl)imidazolidone, N-(3-ethylaminopropyl)-imidazolidone, N-(2-methyl-aminoethyl)uretidinone, N-(2-aminoethyl)hexahydropyrimidinone-2, N-(2-aminoethyl)hexahydro-1,3-diazepinone-2, N-(2-mercaptoethyl)imidazolidone, N-(2-mercaptoethyl)uretidinone, N-(2-mercaptoethyl)hexahydropyrimidinone-2, N-(2-mercaptoethyl)-hexahydro-1,3-diazepinone-2; and the corresponding alkylenethioureas, e.g., N-(2-hydroxyethyl)thioimidazolidone.

A preferred endcapped alkylene oxide polymer useful in the composition of the invention is prepared by endcapping the preferred isocyanate terminated prepolymer described above with N-(2-hydroxyethyl)imidazolidone and has the structure:

oxymethyl-N,N'bisacylalkylenediamines, e.g., N,N'-bismethoxymethyl-N,N'-bisacetylethylenediamine, N,N'-bisbutoxymethyl-N,N'-bisacetylpropylenediamine, N,N',N''-trisalkoxymethyl-N,N',N''-trisacylalkylenetriamines, e.g., N,N',N''-trisacetylethylenetriamine, N,N'-dialkyl-N,N'-bisalkoxymethylpolycarboxamides, e.g., N,N'-dimethyl-N,N'-bismethoxymethylsuccinamide, N,N'-dimethyl-N,N'-bismethoxymethyl adipamide, N,N'-dimethyl-N,N'-bis-methoxymethylphthalamide, and N,N',N''-trimethyl-N,N',N''-trismethoxymethyltrimellitamide; N,N'-dialkyl-N,N'-bisalkoxymethylureas, e.g., N,N'-dimethyl-N,N'-bismethoxyme-

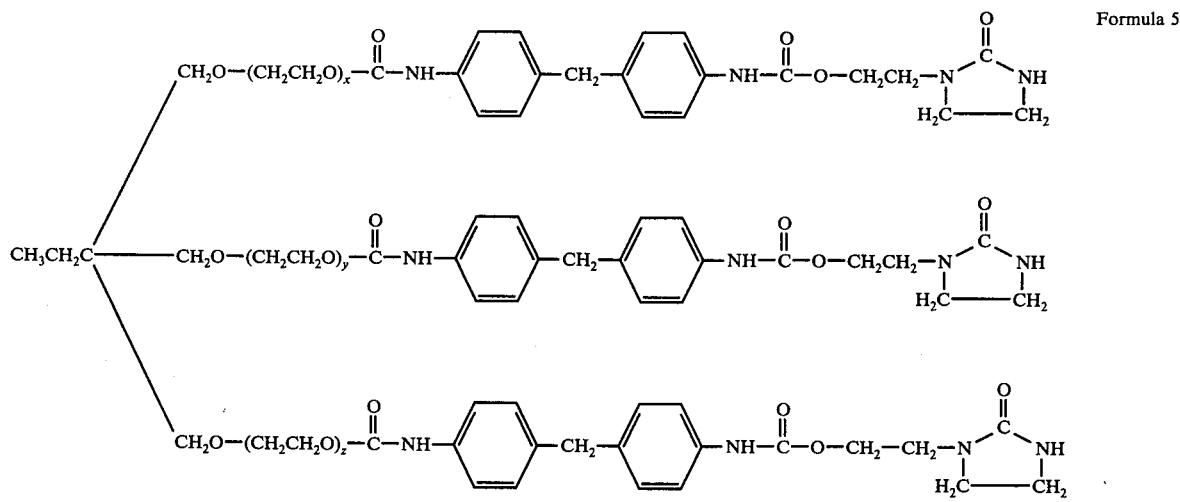

Formula 5

The reaction of the isocyanate-terminated prepolymer and the endcapping compound is carried out under anhydrous conditions in an inert organic liquid solvent, such as dichloromethane, chloroform, benzene or the like. The reaction is exothermic and is generally carried out at a temperature of from about 0° to 100° C., preferably about 25° to 50° C. The use of such solvents permits the control of the reaction temperature to about that of the refluxing solvent. The reaction time is from about 1 hour to 8 hours or more. The reaction time required is determined by the reactivity of the particular prepolymer and endcapping compound used and the reaction temperature used. Completion of the reaction is indicated when a characteristic absorption band, i.e., the isocyanate band, as measured by infrared spectroscopy, disappears.

The crosslinking agents useful for purposes of the present invention are hydrolytically stable compounds which, in the presence of an acid catalyst, react with nucleophilic compounds. Such crosslinking agents include aldehyde polymers, alkoxymethyl derivatives of compounds having at least two acylamide groups, and alkoxymethyl derivatives of compounds having the melamine structure. Examples of such crosslinking agents include, among others, formaldehyde, paraformaldehyde, trioxymethylene, paraldehyde, N,N'-bisalkthylurea, N,N'-dimethyl-N,N'-bisbutoxymethylurea, N-methyl-N'-phenyl-N,N'-bismethoxymethylurea, N,N'-diphenyl-N,N'-bismethoxymethylurea, N,N'-dimethoxymethylurea, N,N,N',N'-tetramethoxymethyurea, N,N,N',N'-tetrabutoxymethylurea, N,N'-dibutoxymethyurea, and N,N'-dihexoxymethylurea; 1,3-bisalkoxymethyluretidionones, e.g., 1,3-bismethoxymethyluretidinone, 1,3-bisalkoxymethyluretidinones, e.g., 1,3-bismethoxymethyluretidinone, and 1,3,-bisbutoxymethyluretininone; 1,3-bisalkoxyimidazolidones, e.g., 1,3-bismethoxymethylimidazolinone, 1,2-bis-1(methoxymethyl)-imidazolidone-2-methoxyethylene, and 1,3-bisalkoxymethyltetrahydro-1,3-diazepinone-2; alkoxymethylmelamines, e.g., hexamethoxymethylmelamine (trade name "Cymel-300" available from the American Cyanamide Co.) pentamethoxymethyl-melamine, tetramethoxymethylmelamine, trimethoxymethylmelamine, dimethoxymethylmelamine and the reaction product of ethylene glycol and hexamethoxymethylmelamine which is a mixture of oligomers, the simplest of which is 1,2-bis[2,4-bis(dimethoxymethylamino)-s-triazinomethoxymethyl-aminomethoxy]-ethylene having the structure:

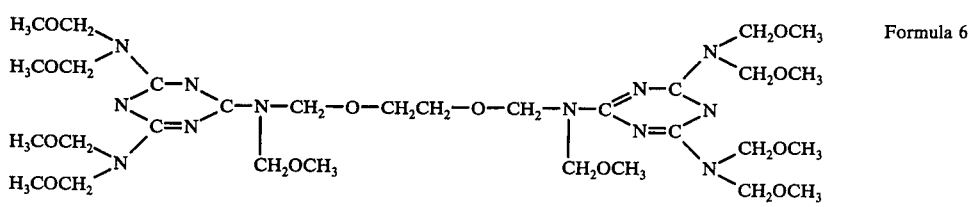

Formula 6

The last named crosslinking agent is the preferred crosslinking agent in the compositions of the invention of the large plurality of crosslinking sites.

The filler materials that may be used in the composition of the invention may be any water insoluble inert solid materials which can provide structural integrity to the molded articles prepared from the composition. A filler is preferred because it helps to impart the properties of toughness, minimal stiffness, and structural stability to the liner. Both inorganic and organic materials and mixtures thereof may be used in the molding composition. Examples of inorganic materials include finely divided oxide and silicate rocks and minerals such as kyanite, staurolite, talc, tremolite, wollastonite, clay mixtures of oxides, e.g., bentonite, finely divided silicon oxides such as sand and colloidal silica, e.g., Cab-O-Sil. Other products include such materials of commerce such as Wollastonite P-L, C-L, and C-6, Microcel E, ASP-103, ASP-400, Micria ZR and Santocel A. Still other useful inorganic materials include flake mica and Hyflo Supercel, titanium dioxide, gypsum, refractaries, colloidal carbon and graphite. Organic fillers that may be used include powders, flakes and fibers of organic polymers such as the nylons, e.g., polyhexamethylenediamine-adipic acid, polyesters, and condensation resins, e.g., phenolformaldehyde resins. Preferred fillers for use in compositions useful for preparation of denture liners are colloidal silicas, an example of which is "Cab-O-Sil M-5" commercially available from the Cabot Corporation.

The cured hydrophilic polymer is a crosslinked structure carrying a filler and water in the matrix of the crosslinked structure. The crosslinked, hydrophilic polymer comprises a plurality of crosslinked segments having the formula

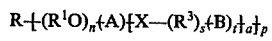

(wherein R, $R^1$, $n$, A, X, $R^3$, B, $s$, $t$, $a$, and $p$ are defined as in Formula 1 hereinabove) and a plurality of crosslinking segments having the formula

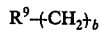

(wherein $R^9$ and $b$ are defined as in Formula 2 hereinabove).

The method of preparing a denture having a soft denture liner thereon comprises, generally, the steps of coating the gum-contacting indented surface of an acrylic denture with a catalyst for the reaction of a polyisocyanate with water followed by coating with an aromatic polyisocyanate primer; placing the molding composition of the invention onto the primed surface; coating a male mold with a release agent, the outer surface of said mold corresponding generally to the surface deviations of said indented surface; closing the denture, the molding composition and the mold in a dental flask; heating the closed flask for about one and one-half (1½) hours at a temperature of at least about 50° C. to cure the molding composition; removing the denture from the dental flask; and finishing the denture by appropriate grinding and polishing.

The following examples, wherein all parts are by weight unless otherwise specified, will further illustrate the present invention.

EXAMPLE 1

Preparation of hydrophilic imidazolidone endcapped polyethylene oxide prepolymers.

A 2-liter resin flask equipped with a reflux condenser dropping funnel, mechanical stirrer, means for maintaining an inert atmosphere, and heating mantle was charged with 355.5 parts polyoxyethylenetriol that had been prepared by condensing ethylene oxide with trimethylolpropane (molecular weight is 1185 and the average value of $n$ in Formula I is 8) and 240 parts dichloromethane. The charged flask was then flushed with dry nitrogen and to it was added, in one portion, 230 parts diphenylmethane-4,4'-diisocyanate (freshly distilled, b.p. 170°–190° C./0.5mm. Hg pressure) in 400 parts dichloromethane.

After the ensuing exotherm had subsided, the mixture was heated to reflux and maintain at this temperature for 8 hours. To the mixture, 121 parts N-(2-hydroxyethyl)imidazolidone as a slurry in 270 parts dichloromethane was added. Reflux was continued for an additional 4 hours during which time the isocyanate band at 4.45 microns, as indicated by infrared spectroscopy, disappeared. This disappearance indicated that the reaction was complete. The mixture was allowed to cool to room temperature, the reflux condenser was replaced by a vacuum distilling head, and the volatiles removed under reduced pressure. About 700 parts of amide-endcapped prepolymer, a pale amber gum-like mass having a molecular weight about 2325 was obtained.

EXAMPLE 2

Example 1 was repeated using 446.4 parts (0.3 moles, 0.9 equivalents) of a polyoxyethylene triol having a molecular weight of 1488 in place of the triol of molecular weight 1185 used in Example 1. About 800 parts amide-endcapped prepolymer as a thick gum-like mass, having a molecular weight of about 2628 was obtained.

EXAMPLE 3

Preparation of crosslinking agent.

Into a 2-liter flask equipped with a stirrer, dropping funnel, thermometer, Dean-Stark trap, and means for maintaining an inert atmosphere in the flask, was placed 1190 parts hexamethoxymethylmelamine ("Cymel-300" commercially available from American Cyanimide Co.). The flask was flushed with nitrogen and the contents heated under nitrogen to melt. While stirring, 38 parts ethylene glycol and 12 parts formic acid was added. The mixture was then stirred and heated at 125° C. for 24 hours during which time about 36 parts methanol distilled and collected in the trap. Upon cooling, a mixture of copolymers of ethylene glycol and hexamethoxymethylmelamine was obtained as a viscous liquid having $\overline{M}n = 530$, $\overline{M}w = 1030$, and $\overline{M}w/\overline{M}n = 1.94$. For purposes of brevity this product was designated HMEG.

EXAMPLE 4

Preparation of a 2 part soft denture liner molding composition.

Part A. About 17.8 parts water was added to 50.6 parts of amide-endcapped prepolymer, prepared as described in Example 1, at about 80° C., and the materials were mixed until a uniform dispersion was obtained. Thereafter, 4.05 parts HMEG, prepared according to Example 3, and, in small portions, 17.2 parts colloidal silica ("Cab-O-Sil" M-5, obtainable from Cabot Corporation) was added. The mixture was thoroughly kneaded in the mixer. A composition having a consistency similar to putty was obtained and thereafter removed from the mixer and stored in a vapor tight container.

Part B. In a similar manner, 50.6 parts of the amide-endcapped prepolymer of Example 1, 17.8 parts water, 1.2 parts 85% phosphoric acid and 7.6 parts of a pink pigment consisting of a 10:1 mixture of "Tipure 901" (obtainable from the DuPont Co) and Williams pure red oxide (obtainable from C. K. Williams Co.) was blended. After the mixture had been mixed to a uniform dispersion, 17.2 parts of colloidal silica was added. This composition had a consistency similar to putty.

EXAMPLE 5

Example 4 was repeated with the exception that the amide-endcapped prepolymer used was that prepared according to Example 2. Both parts A and B of this example had consistencies similar to putty but were slightly more fluid than parts A and B of Example 4.

EXAMPLE 6

To illustrate the various degrees of hardness and water pick-up that may be realized in articles molded from the denture liner molding compositions of the invention, articles were molded of blends of the molding compositions of Examples 3 and 4. The blends, prepared to contain the components as shown in Table 1, were thoroughly mixed by kneading, placed in a metal mold, and cured by heating in an oven at about 95° C. for 2½ hours. The cured samples were weighed, placed in water for 48 hours and reweighed to determine water pickup. Shore A hardness was also measured on samples that had been immersed in water for 48 hours. The results are shown in Table 1 where it will be seen that the hardness varied from a value of 46, for samples containing 100% of the molding compositions of Example 3, down to 28 for samples containing 100% of the molding composition of Example 4. Water pickup for the samples increased from 6.5% to 9.7%. The molded products from each of the blends were hydrophilic, water-extended, filled hydrogels that were tough, soft and form-stable and could readily be machined by cutting and grinding.

Table I

Characteristics of Hydrophilic Molded Products of Crosslinked Amide-Endcapped Prepolymers

| Components of Molding Composition-Parts by Weight | | | | Shore A Hardness | Water Pickup-% |
| --- | --- | --- | --- | --- | --- |
| Ex. 3A | Ex. 3B | Ex. 4A | Ex. 4B | | |
| 50 | 50 | 0 | 0 | 46 | 6.5 |
| 40 | 40 | 10 | 10 | 42 | 7.0 |
| 30 | 30 | 20 | 20 | 38 | 7.5 |
| 20 | 20 | 30 | 30 | 33 | 8.1 |
| 10 | 10 | 40 | 40 | 32 | 9.3 |
| 0 | 0 | 50 | 50 | 28 | 9.7 |

EXAMPLE 7

When the imidazolidone-endcapped prepolymer used in the preparation of the molding composition of Example 4 is replaced by prepolymer prepared in accordance with the procedure of Example 1, using in place of 2-hydroxyethylimidazolidone an equivalent amount of 2-aminoethylimidazolidone, 2-hydroxyethylcarbamate, 2-hydroxyethylurea, acetylethylenediamine or glycinamide, there are obtained molding compositions similar to the molding composition of Example 4. Products molded from these compositions are form-stable and hydrophilic.

EXAMPLE 8

When the prepolymer used in the preparation of the molding compositions of Example 4 is replaced by a prepolymer prepared in accordance with the procedure of Example 1, using in place of the diphenylmethane-4,4'-diisocyanate an equivalent amount of 2,4-toluenediisocyanate, hexamethylene 1,6-diisocyanate, 2,2,5-trimethylhexamethylene-1,6-diisocyanate, or isophoronediisocyanate, there are obtained molding compositions similar to the molding compositions of Example 4. Products molded from these compositions are soft, form-stable and relatively tough.

EXAMPLE 9

Preparation of a 1-part hydrophilic molding composition for denture liners.

To 100 parts of amide-endcapped prepolymer, prepared according to the procedures of Example 1, was added 35 parts water, 7.6 parts of a 10:1 mixture of "Tipure 901" and "Pure Red Oxide R-1599," 4 parts of HMEG, 1 part 2,2,4,4-tetrachloro-3-keto-1,5-pentanediol, latent acid generating catalyst, and the materials mixed in a Mogul mixer at a temperature of about 20° C. until a uniform dispersion was obtained. In small portions, 35 parts of colloidal silica was added and the mixture kneaded in the blender until thoroughly mixed. A pink colored hydrophilic molding composition having a putty-like consistency was obtained. By pressing the molding composition in metal molds and heating the molds in an oven at about 90° C. for 2½ hours, hydrophilic molded products were obtained. These products, after soaking in water for 48 hours, gained 7.0% in weight and had a Shore A hardness of 46.

EXAMPLE 10

Example 9 was repeated using the amide-endcapped prepolymer described in Example 2 in place of the amide-endcapped prepolymer of Example 1. A hydrophilic molded product was obtained that, after soaking in water for 48 hours, gained 10% in weight and had a Shore A hardness of 28.

EXAMPLE 11

Lining of a denture with a soft denture liner of the present invention.

An acrylic denture (upper) was invested in a dental flask and an upper mold made so as to leave room for the soft liner on the surface of the denture. The contacting surface of the denture was roughened by sanding and was primed to improve adhesion of the denture to the dental liner by swabbing with a solution of 5% butyl tin trichloride in 60:40 tetrahydrofuran:water and the solvent allowed to evaporate. The surface was then swabbed with a 25% solution of "Papi," a polymethylene polyphenylisocyanate available commercially from the Upjohn Company, in chloroform to give a uniform coating and allowed to dry for 10 minutes.

Equal parts of A and B of hydrophilic molding composition similar to that of Example 4, but containing 30 parts water and 32.8 parts colloidal silica per 100 parts of amide-endcapped prepolymer, were thoroughly mixed by kneading for about 3 minutes. The mixed molding composition was spread over the upper surface of the denture, the top mold was painted with a silicone release agent ("Modern Foil") available from Modern Materials Manufacturing Co., St. Louis, Mo.) and the mold was pressed in a hydraulic press until the mold was closed. The closed dental flask was then clamped and placed in a 100° C. water bath for 1½ hours to cure the molding composition. The flask was then placed in cold water for about 5 minutes and the lined denture removed from the mold. The lined denture was finished by grinding the excess soft liner from the denture using a "Fast-Cut" stone followed by coarse sanding wheel. The liner was then buffed with pumice.

On soaking in water for 48 hours, the denture liner gained about 4% in weight. This weight gain was insufficient to change the dimensions of the denture liner significantly enough to alter the fit of the denture in the mouth. The liner adhered tenaciously to the denture and provided a firm and comfortable fit to the alveolar ridge of the user. Test samples molded of the same molding composition used in making this denture liner were found to contain about 32% water at equilibrium in water and exhibited a Shore A hardness of about 40, a tensile strength of 320 psi. and elongation at break of about 120%.

Adhesion of the hydrophilic denture liners of the invention to the acrylic surface of dentures is poor without use of a primer coating on the acrylic denture surface. Excellent adhesion is provided by primer coatings comprising aromatic polyisocyantes. Included among the aromatic polyisocyantes useful as primer coatings are "Papi," the polymethylene polyphenyleneisocyanate manufactured by the Upjohn Company and used in Example 11; "Isonate" 901, a polymethylene polyphenyleneisocyanate with an isocyanate equivalent weight different from "Papi" and also manufactured by the Upjohn Company; diphenylmethane-4,4'-diisocyanate; and diphenylmethane-4,4'-dimethyl-3,3'-diisocyanate. "Papi" is a preferred aromatic polyisocyanate for use as a primer coating. Catalysts which accelerate the reaction of isocyanates may also be used, including for example compounds such as stannic chloride, butyl tin trichloride, dibutyl tin dichloride, tributyl tin acetate, triethylene diamine, etc. A preferred catalyst is butyl tin trichloride. Usually, the primer and its catalyst is applied to the acrylic surfaces as a solution in an inert solvent, e.g., chloroform, carbon tetrachloride, tetrahydrofuran, etc.

EXAMPLE 12

Preparation of a new denture with a soft denture liner of the invention.

Artificial teeth were positioned in a denture mold for a lower denture and a sufficient amount of an acrylic denture base added to the mold to form the denture. A wax shim of the correct thickness for a soft denture liner was placed in a male mold that had been prepared from an impression of the alveolar ridge of an edentulous patient and the male mold positioned in the denture mold. The acrylic base was partially cured by placing the closed dental flask in a 75° C. water bath for about 5 minutes. The flask was opened, the wax shim removed and the acrylic surface cleaned thoroughly with boiling water followed by swabbing with methyl methacrylate, and coating the alveolar ridge male mold with a release agent.

The partially cured acrylic denture was primed with an aromatic polyisocyanate ("Papi") the mold charged with hydrophilic denture liner molding composition, closed, and cured as in Example 11. The lined denture was finished by grinding with a "Fast-Cut" stone, a coarse sanding wheel and a fine sanding wheel. It was then buffed and finally polished. The liner adhered tenaciously to the denture and provided a firm, dimensionally stable, comfortable fit to the alveolar ridge of the user.

EXAMPLE 13

Illustration of the effect of cross linking agent on the properties of molded products prepared from amide-endcapped prepolymers.

Table 2 gives the tensile strength and elongation at break of molded products prepared from various amide-endcapped prepolymers and cross linking agents. In Table 2, A refers to an amide-endcapped prepolymer prepared as in Example 1, B to an amide-endcapped prepolymer prepared as in Example 2, and C to a prepolymer prepared as in Example 1 using an equivalent amount of tolylene diisocyanate in place of diphenylmethane-4,4'-diisocyanate. It may be seen by inspection of Table 2 that increase in cross linking agent results in an increase in the wet and dry tensile strengths and a decrease in the wet and dry elongation for molded products prepared from the amide-endcapped prepolymer described in Example 1. It may also be seen that with equivalent amounts of the same cross linking agent, prepolymer A gives molded products having higher tensile strengths both dry and wet than prepolymer B which has a higher ethylene oxide content. Furthermore, it may be seen that both wet and dry tensile strengths of prepolymer C, a prepolymer containing tolylene diisocyanate moieties are lower than the wet and dry tensile strengths of similar prepolymers containing diphenylmethane-4,4'-diisocyanate moieties.

Table 2

Physical Properties of Molded Products

| Prepolymer | Cross Linking Agent - (Wt.%) | Tensile Strength-psi Dry | Wet | % Elongation Wet | Dry |
|---|---|---|---|---|---|
| C | HMM (5) | 130 | 50 | 70 | 30 |
| C | HMEG (5) | 180 | 60 | 100 | 30 |
| A | HMM (5) | 200 | 80 | 90 | 40 |
| A | HMEG (5) | 250 | 140 | 90 | 40 |
| B | HMM (5) | 190 | 70 | 110 | 40 |
| B | HMEG (5) | 220 | 120 | 90 | 40 |
| A | HMM (25) | 2200 | 590 | 40 | 10 |
| A | HMEG (25) | 2470 | 790 | 40 | 10 | wherein HMM is hexamethoxymethylmelamine and HMEG is the reaction product of hexamethoxymethylmelamine and ethylene glycol as described in Example 3.

What is claimed is:

1. A composition useful for the preparation of soft, tough, hydrophilic articles, comprising:
   (a) about 100 parts by weight of an amide-endcapped hydrophilic alkylene oxide prepolymer having the formula

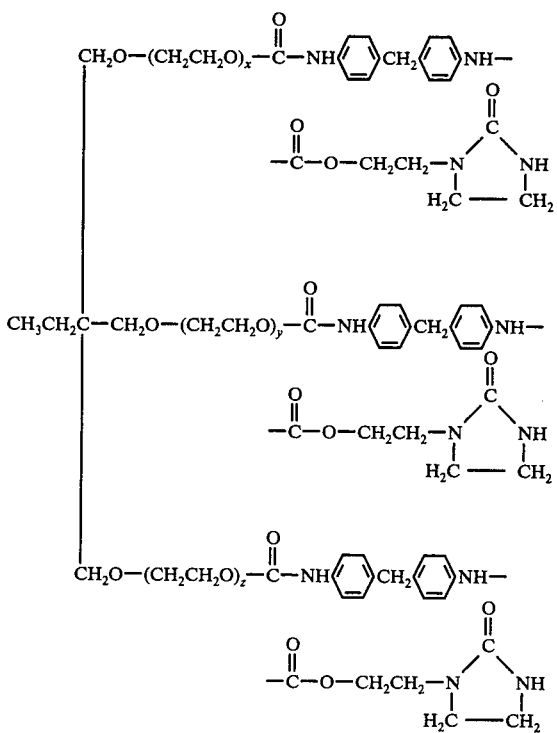

wherein x, y and z are integers of from 5 to 25;
  (b) from 2 to 8 parts of an acid activated cross linking agent which is a compound having the formula

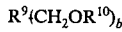

wherein $R^9$ is a polyvalent organic nitrogeneous residue selected from the group consisting of

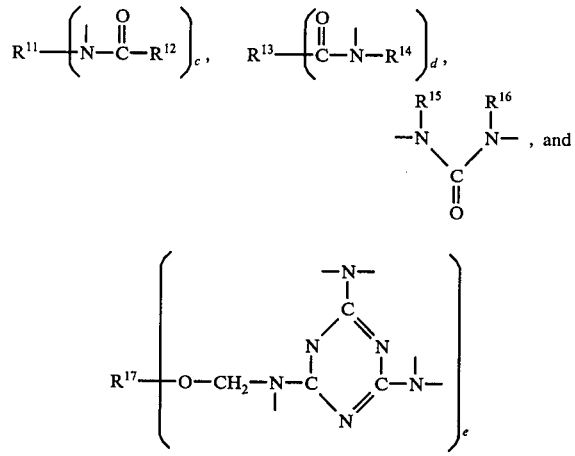

wherein $R^{11}$ and $R^{13}$ are polyvalent organic residues having a combining valency of c and d respectively; c and d are integers having a value of from 2 to 4; $R^{12}$, $R^{14}$, $R^{15}$, and $R^{16}$ are selected from the group consisting of hydrogen and lower alkyl groups having from 1 to 6 carbon atoms, and $R^{14}$ and $R^{15}$ together may form a ring with the nitrogen atom having 4 to 7 atoms therein; $R^{17}$ is a polyvalent radical of an organic polyhydroxy alkyl compound having e hydroxyl groups but devoid of such groups, e is an integer from 1 to 6; and where e is 1, $R^{17}$ is a lower alkyl group having from 1 to 6 carbon atoms;

$R^{10}$ is a lower alkyl group having from 1 to 6 atoms; and b is an integer from 2 to 6;
  (c) from 20 to 50 parts by weight of water;
  (d) from 20 to 45 parts by weight of a suitable filler; and
  (e) from 0.1 to 3 parts by weight of a catalyst selected from the group consisting of acids having a $pK_a$ less than 4, and latent acid generating compounds capable of generating an acid having a $pK_a$ less than 4 upon heating at a temperature of at least 50° C.

2. The molding composition of claim 1 wherein x, y, and z are integers having a value of from 8 to 10.

3. The molding composition of claim 1 wherein the acid activated crosslinking agent is a reaction product of hexaalkoxymethylmelamine, wherein the alkyl group has from 1 to 6 carbon atoms, and an ethylene glycol.

4. The molding composition of claim 3 wherein the hexaalkoxymethylmelamine is hexamethoxymethylmelamine.

5. The composition of claim 1 wherein said catalyst is a latent acid generating compound which is 2,2,4,4-tetrachloro3-keto-1,5-pentanediol.

6. A two-part molding composition useful for the preparation of water-extended, tough, soft, form-stable hydrophilic articles by reacting Part A with Part B, comprising Parts A and B, wherein Part A comprises:
  (a) from 25 to 75 parts by weight of a hydrophilic amide end-capped prepolymer having the formula

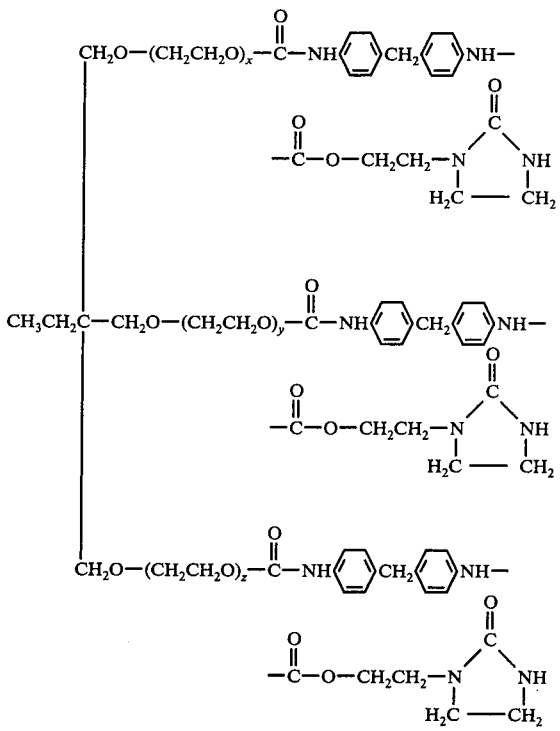

wherein x, y and z are integers of from 5 to 25,
  (b) from 0.25 to 0.50 parts by weight water per part of prepolymer,
  (c) from 0.20 to 0.45 parts by weight of filler per part of prepolymer, and
  (d) from 0.1 to 3 parts by weight per 100 parts of molding composition of a catalyst selected from the group consisting of acids having a $pK_a$ less than 4 and latent acid generating compounds capable of generating an acid having a $pK_a$ less than 4 upon heating to a temperature of at least 50° C.; and Part B comprises:

(e) from 75 to 25 parts by weight of a hydrophilic amide end-capped prepolymer, as defined in (a);

(f) from 0.25 to 0.50 parts by weight of water per part of prepolymer, (g) from 0.20 to 0.45 parts by weight of filler per part of prepolymer, and (h) 2 to 8 parts by weight of a cross-linking agent which is the reaction product of hexaalkoxymethylmelamine, wherein the alkyl group has from 1 to 6 carbon atoms, and an ethylene glycol.

* * * * *